(12) United States Patent
Fujiwara et al.

(10) Patent No.: US 6,244,864 B1
(45) Date of Patent: Jun. 12, 2001

(54) TEETH MARK IMPRESSION RECORDING MEMBER AND METHOD FOR USING THE SAME

(75) Inventors: Toshihisa Fujiwara, Atsugi; Hironobu Tsuji, Tokyo, both of (JP)

(73) Assignees: Nissan Digital Process Ltd., Atsugi; Media Corporation, Tokyo, both of (JP)

(*) Notice: Subject to any disclaimer, the term of this patent is extended or adjusted under 35 U.S.C. 154(b) by 0 days.

(21) Appl. No.: 09/576,387

(22) Filed: May 22, 2000

Related U.S. Application Data

(63) Continuation of application No. PCT/JP99/05173, filed on Sep. 22, 1999.

(30) Foreign Application Priority Data

Sep. 24, 1998 (JP) .................................................. 10-307774

(51) Int. Cl.$^7$ ........................................................ A61C 9/00
(52) U.S. Cl. .............................. 433/71; 433/48; 433/214
(58) Field of Search .................................. 433/71, 70, 37, 433/48, 214

(56) References Cited

U.S. PATENT DOCUMENTS

| | | | |
|---|---|---|---|
| 4,768,951 | * | 9/1988 | Abiru et al. ............................ 433/48 |
| 4,786,254 | * | 11/1988 | Millstein et al. ....................... 433/71 |
| 5,346,395 | * | 9/1994 | Adell ...................................... 433/71 |
| 5,487,662 | * | 1/1996 | Kipke et al. ............................ 433/37 |

FOREIGN PATENT DOCUMENTS

| | | |
|---|---|---|
| 2-138106 | 5/1990 | (JP) . |
| 3-9744 | 1/1991 | (JP) . |
| 5-155732 | 6/1993 | (JP) . |

* cited by examiner

*Primary Examiner*—Gene Mancene
*Assistant Examiner*—Melba Bumgarner
(74) *Attorney, Agent, or Firm*—Kanesaka & Takeuchi

(57) ABSTRACT

The present invention provides a teeth mark impression recording member, the teeth mark impression recording member may improve a measuring accuracy of an ideal diffusion-type laser light system and has excellent properties in fixing the member into the abutment teeth and includes a fixing part for fixing and sticking the member into abutment teeth, and an impression recording part for recording an impression of the opposing teeth, and at least the impression recording part includes reflection modifier as an additive.

12 Claims, 3 Drawing Sheets

TEETH MARK IMPRESSION RECORDING MEMBER AND METHOD FOR USING THE SAME

CROSS REFERENCE TO RELATED APPLICATION

This is a continuation application of PCT International Application of PCT/JP99/05173 filed on Sep. 22, 1999.

TECHNICAL FIELD

The present invention relates to a teeth mark impression recording member. The teeth mark impression recording member is used for dental operations, such as dental prosthesis of the crown, bridging, and the like, which use a dental CAD/CAM equipment. The teeth mark impression recording member is used to record shapes and tracks of opposing teeth during chewing (which may be called "an occlusal record" or "a teeth mark impression".).

BACKGROUND ART

Up to now, a single-layer teeth mark impression recording member, which uses polyethylene wax and the like, having plasticity, is known. The teeth mark impression recording member is used to record shapes and tracks of opposing teeth by inserting the member into an oral cavity and by chewing the teeth mark impression recording member back and forth, right and left and the like.

However, the teeth mark impression recording member of the prior art which is made from polyethylene wax has the following problems.

(1) In case of the recording tracks of teeth which move in al directions dynamically, such as in chewing situation, the teeth mark impression recording member tends to move to the different position which are predetermined and to float from the teeth. As a result, the teeth mark impression of the opposing teeth may have an error.

Accordingly, the hardened teeth mark impression recording member has been made. In accordance with the attempt, however, it becomes difficult to fix and stick the member into teeth, and thereby it is not easy to obtain a teeth mark impression of the opposing teeth accurately.

(2) After recording a teeth mark impression, when the teeth mark impression recording member is taken out from the oral cavity, the record in the impression recording part may be easily deformed. In accordance with the previous teeth mark impression recording member, therefore, the member must be treated so carefully and it is difficult to maintain the teeth mark impression for a certain period of time.

(3) Further, when three dimensional data is taken from the teeth mark impression, which is recorded by the previous teeth mark impression recording member, owing to insufficiencies of hardness and rigidity, it is difficult to measure the shape of the teeth mark impression by using a contact measuring system.

Accordingly, using an ideal diffusion-type laser light system has beem proposed. In accordance with the proposal, however, in irradiating the laser light onto the teeth mark impression recording member consisting of a polyethylene wax, the laser light transmits, spreads or internally reflects in one direction only, and thereby it is difficult to measure the teeth mark impression accurately.

Under the circumstances, the present invention, i.e. such a teeth mark impression recording member and a method for using the same has an excellent reflective property with an ideal diffusion-type laser light system by constituting the teeth mark impression recording member which comprises a fixing part for fixing and sticking the member into abutment teeth, and a impression recording part for recording an impression of opposing teeth, wherein at least the impression recording part includes a reflection modifier as an additive.

DISCLOSURE OF THE INVENTION (1) The present invention provides a teeth mark impression recording member comprising a fixing part for fixing and sticking the member into teeth and an impression recording part for recording an impression of opposing teeth, wherein at least the impression recording part includes a reflection modifier.

By constituting a teeth mark impression recording member like this, the above-mentioned problems can be solved. In accordance with the present invention, therefore, when a laser light is irradiated onto the impression recording part of the teeth mark impression recording member, due to the reflection modifier, the part may reflect the uniformly diffused laser light. Therefore, by detecting the uniformly diffused laser light, three-dimensional teeth mark impression, which was recorded in the teeth mark impression recording member, may be measured accurately.

Further, the fixing part of the teeth mark impression recording member in accordance with the present invention is fixed and stuck into abutment teeth etc., and the impression recording part is bonded to the fixing part. Therefore, if opposing teeth moves sideways or in front and back directions, due to the rigidity of the fixing part, movement of the impression recording part is restricted effectively. As a result, due to the impression recording part, it is easy to obtain a teeth mark impression of the opposing teeth having an excellent accuracy.

(2) In accordance with the teeth mark impression recording member of the present invention, as the reflection modifier, it is preferable to use at least one compound selected from the group consisting of titanium oxide, silicon oxide, aluminum oxide, zirconium oxide, indium oxide, tin oxide, zinc oxide, antimony oxide, yttrium oxide, cobalt oxide, barium sulfate, sodium sulfate, calcium carbonate, sodium carbonate, carbon, a carbon black, a glass fiber and a carbon fiber.

By using the reflection modifier, relatively small addition of the modifier may exhibit an excellent reflection modifying effect. In other word, by using the reflection modifier, since the irradiated laser light is uniformly diffused and then reflected, the transmittance, the spreading and the internal reflection in only one direction of the laser light are effectively inhibited.

(3) In accordance with the teeth mark impression recording member of the present invention, the reflection modifier is preferably included in the range of 0.01 to 80 weight % of the whole amount.

Since the reflection modifier is included in the above range, a predetermined reflection modifying effect may be obtained with maintaining an excellent impression recording ability of the impression recording part.

(4) In accordance with the teeth mark impression recording member of the present invention, the glass transition temperature of the fixing part is preferably higher than the glass transition temperature of the impression recording part. In other word, where the glass transition temperature of the fixing part is Tg1, and the glass transition temperature of the impression recording part is Tg2, it is preferable that the relationship "Tg1>Tg2" is met.

Since the relationship of the glass transition temperatures is met, better balance of the impression recording ability and the fixing and sticking abilities can be obtained.

The glass transition temperature of the resin may be measured, for example by using a DSC method, at the heating speed of 10° C./min under the nitrogen stream atmosphere, as a changing point of specific heat.

(5) In accordance with the teeth mark impression recording member of the present invention, the Shore A hardness (according to JIS K6301) of the resin used for the fixing part is preferably higher than the Shore A hardness of the resin used for the impression recording part. In other word, where the Shore A hardness of the resin used for the fixing part is SA1, and the Shore A hardness of the resin used for the impression recording part is SA2, it is preferable that the relationship "SA1>SA2" is met.

Since the relationship of the Shore A hardnesses is met, better balance of the impression recording ability and the fixing and sticking abilities may be obtained.

The Shore A hardness of the resin may be measured according to JIS K6301 standard.

(6) In accordance with the teeth mark impression recording member of the present invention, the melting point of the resin used for the fixing part is preferably higher than the melting point of the resin used for the impression recording part. In other word, where the melting point of the resin used for the fixing part is Mp1, and the melting point of the resin used for the fixing impression recording part is Mp2, it is preferable that the relationship "Mp1>Mp2" is met.

Since the relationship of the melting point is met, better balance of the impression recording ability and the fixing and sticking abilities may be obtained.

The melting point of the resin may be measured, for example by using a DSC method, as a peak melting temperature.

(7) In accordance with the teeth mark impression recording member of the present invention, the softening point of the resin used for the fixing part is preferably higher than the softening point of the resin used for the impression recording part. In other word, where the softening point of the resin used for the fixing part is Sp1, and the softening point of the resin used for the impressive recording part is Sp2, it is preferable that the relationship "Sp1>Sp2" is met.

Since the relationship of the softening points is met, better balance of the impression recording ability and the fixing and sticking abilities may be obtained.

The softening point of the resin may be measured, for example by using the falling-sphere viscometer.

(8) In accordance with the teeth mark impression recording member of the present invention, each of the resins used for the fixing part and the impression recording part preferably comprises;

a high molecular weight part having a number-average molecular weight of 100,000 or greater, and a low molecular weight part having a number-average molecular weight of less than 100,000, wherein the content of the high molecular weight part, which is included in the resin used for the fixing part, is 50 weight % or greater, and the content of the high molecular weight part, which is included in the resin used for the impression recording part, is less than 50 weight %.

By using the above-mentioned resins, therefore, same kind of resins may be used for the fixing part and for the impression recording part. Further, the fluidity of these resins may be controlled easily, and excellent qualities of impression recording ability and fixing ability may be obtained.

(9) In accordance with the teeth mark impression recording member of the present invention, a temperature indicating material is preferably included in the fixing part and/or the impression recording part.

By using the above-mentioned material, therefore, excessive heating of the teeth mark impression recording member may be inhibited before using the member in an oral cavity.

(10) In accordance with the teeth mark impression recording member of the present invention, a supporting layer is preferably provided between the fixing part and the impression recording part.

By using the above-mentioned supporting layer, therefore, treatment of the teeth mark impression recording member may be easier. In addition, since variety of resins may be used, more excellent fixing ability of the fixing part and more excellent impression recording ability of the impression recording part may be obtained.

(11) The present invention provides another embodiment which is a method for using the teeth mark impression recording member, comprising the steps of;

heating the teeth mark impression recording member as mentioned above, recording tracks of opposing teeth by inserting the teeth mark impression recording member into an oral cavity, and measuring the tracks of opposing teeth, which was already recorded in the recording step, by using an ideal diffusion-type laser light system.

BEST MODE FOR CARRYING OUT THE INVENTION

The first embodiment in accordance with the present invention (the teeth mark impression recording member), the second embodiment (the teeth mark impression recording member including the supporting part), and the third embodiment (the method for using the teeth mark impression recording member) will be described with reference to the appropriate drawings.

[The First Embodiment]

Figure 1:
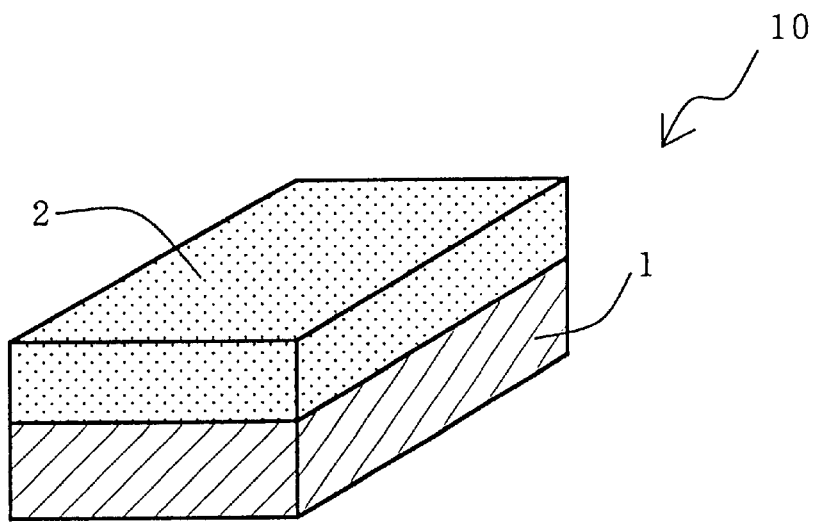
FIG. 1 shows a perspective view of the teeth mark impression recording member in accordance with the first embodiment of the present invention.

As shown in FIG. 1, the first embodiment in accordance with the present invention is the teeth mark impression recording member 10. The member 10 comprises the fixing part 1 for fixing and sticking the member into the abutment teeth and the adjacent teeth, and the impression recording part 2 for recording an impression of the opposing teeth, and at least the impression recording part 2 includes a reflection modifier.

In accordance with the impression recording member 10, both of the fixing part 1 (which may be called "the first layer"), and the impression recording part 2 (which may be called "the second layer") may be maintained in a predetermined shapes at a room temperature and may be softened, above a predetermined temperature, to show plasticity, and may be deformed according to a given pressure.

In other word, the fixing part 1, may be fixed and stuck into the abutment teeth and the adjacent teeth, and the impression recording part 2, may record the status and tracks of the chewing surface of the opposing teeth. Further, softening degree of the fixed part 1 is smaller than softening degree of the impression recording part 2. Therefore, due to the fixing part 1, movement of the impression recording part 2 during recording may be restricted and thereby the teeth mark impression may be recorded quickly and accurately. Further, the teeth mark impression recording member 10 comprises the fixing part 1 and the impression recording part 2. Therefore, after recording the teeth mark impression, the impression recording part 2 may be easily detached from the opposing teeth and the abutment teeth etc. and thereby the teeth mark impression recording member 10 may be taken out from an oral cavity.

In addition, the impression recording part 2 includes a reflection modifier. Therefore, irradiated laser light may be uniformly diffused and then reflected, and thereby the tracks of the opposing teeth, which was already recorded, may be measured accurately by using the ideal diffusion-type laser light system.

(1) The Fixing Part
i) Resin

The resin used for the fixing part is not restricted. The resin may be the resin or combination of resins, selected from the group consisting of a polyethylene resin, a polypropylene resin, a polymethylpentene resin, a (meth)acrylic resin, a silicone resin, a polyvinyl acetate resin, a polyethylene-vinyl acetate resin, a polyvinyl butyral resin, a polyvinyl formal resin, a polyvinyl alcohol resin, cellulose acetate, ethyl cellulose, a polycaprolactone resin, a polyurethane resin, a styrene-butadiene resin, styrene-butadiene-styrene block polymer resin, a styrene-isoprene-styrene block polymer resin, a styrene-butylene-ethylene-styrene block polymer resin, a phenoxy resin, and the like.

Among those resins, resins that include a hydroxyl group or a carboxyl group as a functional group are preferable. For example, a silicone resin, a polyvinyl acetate resin, a polyethylene-vinyl acetate resin, a polyvinyl butyral resin, a polyvinyl formal resin, a polyvinyl alcohol resin, cellulose acetate, ethyl cellulose, a polyester resin, a (meth)acrylic resin, and the like, are preferable. As mentioned above, a functional group having a higher polarity may improve fixing and sticking abilities into the abutment teeth.

Further, as the resin used for the fixing part, at least one resin selected from the group consisting of a polyvinyl acetate resin, a polyethylene-vinyl acetate resin, and a polycaprolactone resin is more preferable.

ii) Crosslinked Resin

As the resin used for the fixing part, a crosslinked resin may be preferably used. For example, the above resin having a hydroxyl group may be preferably crosslinked by a crosslinking agent, such as an isocyanate compound, a dicarboxylic acid compound, an epoxy compound, and the like. For example, the above resin having a carboxyl group may be preferably cross-linked by a crosslinking agent, such as an epoxy compound, an acidic anhydride, a dihydroxy compound, and the like.

By crosslinking the resin like this, the controlling of the glass transition temperature(Tg) of a cured resin may become easier, and thereby the fixed part may be fixed and stuck into teeth well and deformation of the impression recording part after recording may be inhibited more easily.

iii) Molecular Weight

The molecular weight of the resin used for the fixing part is not restricted. For example, the number-average molecular weight in term of polystyrene (Mn), measured by the gel permeation chromatography (GPC), is preferably in the range of 10,000 to 500,000.

The reasons are as follows. When the number-average molecular weight of the resin is less than 10,000, it may be difficult to fix and stick the member into the abutment teeth etc. On the other hand, when the number-average molecular weight of the resin is greater than 500,000, softening ability during heating process is insufficient and thereby it may be difficult to fix and stick the member into the abutment teeth.

In order to fix and stick the member more easily, therefore, the number-average molecular weight is more preferably in the range of 30,000 to 300,000, and is furthermore preferably in the range of 50,000 to 200,000.

Further, the resin used for the fixing part is preferably the resin which consists of a combination of a high molecular weight part having a number-average molecular weight of 100,000 or greater, and a low molecular weight part having a number-average molecular weight of less than 100,000, wherein the content of the high molecular weight part included in the resin is 50 weight % or greater.

In accordance with the above-mentioned resin, therefore, the high molecular weight part may make the fixing part rigid and thereby movement of the impression recording part may be restricted. Further, the low molecular weight part may improve sticking ability into the abutment teeth etc.

In case of using the above-mentioned resin as the fixing part, the resin used for the impression recording part is preferably the resin which consists of a combination of a high molecular weight part having a number-average molecular weight of 100,000 or greater, and a low molecular weight part having a number-average molecular weight of less than 100,000, wherein the content of the high molecular weight part included in the resin, is less than 50 weight %.

As the combination of the resins is used for the fixing part and the impression recording part, the impression recording ability of the impression recording part may be improved. Further, as the same kind of resins may be used for the fixing part and the impression recording part, the bonding quality between the fixing part and the impression recording part may be improved.

iv) Glass Transitions Temperature

The glass transition temperature of the resin used for the fixing part is preferably in the range of −30 to 70° C.

The reasons are as-follows. When the glass transition temperature is lower than −30° C., it may be difficult to maintain the shape at a room temperature and to fix and stick the member into the abutment teeth etc. On the other hand, when the glass transition temperature is higher than 70° C., softening ability during heating process becomes insufficient and thereby it may be difficult to fix and stick the member into the abutment teeth etc.

In order to fix and stick the member more easily, therefore, the glass transition temperature is more preferably in the range of −20 to 50° C., and is furthermore preferably in the range of −10 to 30° C.

Further, it is also preferable to determine the glass transition temperature (Tg1) of the resin used for the fixing part considering the glass transition temperature (Tg2) of the resin used for the impression recording part. In that case, it is preferable that the relationship "Tg1>Tg2" is met, and it is more preferable that the relationship "Tg1>Tg2+10° C." is met.

v) Shore A Hardness

The Shore A hardness (according to JIS K6301) of the resin used for the fixing part is preferably in the range of 80 to 100°.

The reasons are as follows. When the Shore A hardness is lower than 80°, it may be difficult to maintain the shape at a room temperature and to fix and stick the member into the abutment teeth etc. On the other hand, when the Shore A hardness is higher than 100°, softening ability during heating process becomes insufficient and thereby it may be difficult to fix and stick the member into the abutment teeth etc.

In order to fix and stick the member more easily, therefore, the Shore A hardness is more preferably in the range of 85 to 95°.

Further, it is also preferable to determine the Shore A hardness (SA1) of the resin used for the fixing part considering the Shore A hardness (SA2) of the resin used for the impression recording part. In that case, it is preferable that the relationship "SA1>SA2" is met, and it is more preferable that the relationship "SA1>SA2+5°" is met.

vi) Melting Point

The melting point of the resin used for the fixing part is preferably in the range of 150 to 250° C.

The reasons are as follows. When the melting point is lower than 150° C., it may be difficult to maintain the shape at a room temperature and to fix and stick the member into the abutment teeth etc. On the other hand, when the melting point is higher than 250° C., softening ability during heating process becomes insufficient and thereby it may be difficult to fix and stick the member into the abutment teeth etc.

In order to fix and stick the member more easily, therefore, the melting point is more preferably in the range of 160 to 240° C., and is furthermore preferably in the range of 170 to 230° C.

Further, it is also preferable to determine the melting point (Mp1) of the resin used for the fixing part considering the melting point (Mp2) of the resin used for the impression recording part. In that case, it is preferable that the relationship "Mp1>Mp2" is met, and it is more preferable that the relationship "Mp1>Mp2+30° C." is met.

vii) Softening Temperature

The softening temperature of the resin used for the fixing part is preferably in the range of 60 to 100° C.

The reasons are as follows. When the softening temperature is lower than 60° C., it may be difficult to maintain the shape at a room temperature and to fix and stick the member into the abutment teeth etc. On the other hand, when the softening temperature is higher than 100° C., softening ability during heating process becomes insufficient and thereby it may be difficult to fix and stick the member into the abutment teeth etc.

In order to fix and stick the member more easily, therefore, the softening temperature is more preferably in the range of 65 to 95° C., and is furthermore preferably in the range of 70 to 90° C.

Further, it is also preferable to determine the softening temperature (Sp1) of the resin used for the fixing part considering the softening temperature (Sp2) of the resin used for the impression recording part. In that case, it is preferable that the relationship "Sp1>Sp2" is met, and it is more preferable that the relationship "Sp1>Sp2+10° C." is met.

viii) Additives

Various kinds of additives may be preferably included in the resin used for the fixing part. For example, a compound or a combination of compounds, selected from the group consisting of a polymer additive, a reactive dilution agent, a radical-type polymerization initiator, a polymerization inhibitor, a polymerization initiator auxiliary, a levelling agent, wettability modifier, a surfactant, a plasticizer, a lubricant, an ultraviolet absorber, an anti-oxidation agent, an anti-static spray, an inorganic filler, a fungicide, moisture conditioner, a dye-dissolution agent, a buffer solution, a chelating agent, an antimicrobal agent, a perfume, and the like, may be preferably used.

Especially, a stearic acid or a palmitic acid as a lubricant, or dibutyl phthalate etc. as a plasticizer may be preferably included in the resin. As such an additive is included in the resin, fixing and sticking ability into the fixing part may be improved and after recording the teeth mark impression, the fixing part may be easily detached from the teeth.

Further, a fungicide also may be preferably included in the resin. As the resin includes the fungicide, anti-fungous catalytic action may be exhibited easily and thereby become more sanitary.

ix) Shape

With respect to the thickness of the fixing part, it is necessary to fill the resin between the abutment teeth etc. and thereby to fix and stick the member into the teeth. The thickness of the fixing part is not restricted. For example, the thickness may be preferably in the range of 0.5 to 10 mm.

The reasons are as follows. When the thickness of the fixing part is smaller than 0.5 mm, it may be difficult to fix and stick the member into the abutment teeth etc. and to hold the impression recording part. On the other hand, when the thickness of the fixing part is larger than 10 mm, usability may become deteriorated and fabrication may become difficult.

Therefore, the thickness of the resin used for the fixing part may be more preferably in the range of 1 to 8 mm, and furthermore preferably in the range of 2 to 5 mm.

Further, it is also preferable to provide a thickness controlling layer between the fixing part and the impression recording part or on the surface of the fixing part. According to the above-mentioned construction, therefore, when each of the abutment teeth has a different height or each of the space between the abutment teeth and the adjacent teeth has different sizes, the fixing part and the thickness controlling layer may be easily deformed and filled in the spaces. Therefore, the impression recording part may be more flat and thereby the teeth mark impression of the opposing teeth may be recorded more accurately.

The size of the fixing part is not restricted. For example, the fixing part may be a rectangle having 10 to 30 mm in length and 10 to 30 mm in width or a circle having 10 to 30 mm in diameter. Further, according to the application, the fixing part may be preferably a triangle, a pentagon, or an ellipse.

(2) The Impression Recording Part i) Resin

With respect to the resin used for the impression recording part, the above-mentioned resin which is usable for the fixing part, may be used as well. Therefore, the resin may be a resin or combination of resins, selected from the group consisting of a polyethylene resin, a polypropylene resin, a polyvinyl acetate resin, a polyethylene-vinyl acetate resin, a polyvinyl butyral resin, a polyvinyl formal resin, a polyvinyl alcohol resin, cellulose acetate, and the like.

ii) Crosslinked Resin

As the resin used for the impression recording part the crosslinked resin may also be preferable as same as the fixing part in order to improve the creep-resistant ability.

For example, a resin having a hydroxy group may be preferably crosslinked by a crosslinking agent, such as an isocyanate compound, a dicarboxylic acid compound, an epoxy compound, and the like. For example, a resin having a carboxyl group may be preferably crosslinked by a crosslinking agent, such as an epoxy compound, an acidic anhydride, an dihydroxy compound, and the like.

iii) Molecular Weight

The molecular weight of the resin used for the impression recording part is not restricted. For example, the number-average molecular weight in term of polystyrene (Mn), measured by GPC, is preferably smaller than that of the resin used for the fixing part and is preferably in the range of 10,000 to 300,000.

The reasons are as follows. When the number-average molecular weight of the resin is less than 10,000, the creep-resistance may become low. On the other hand, when the number-average molecular weight of the resin is greater than 300,000, softening ability during heating is insufficient and thereby it may be difficult to record the teeth mark impression, including the tracks of the opposing teeth, accurately. Further, since the number-average molecular weight of the impression recording part is smaller than the number-average molecular weight of the fixing part, the resin used for the impression recording part may be deformed more easily and thereby the teeth mark impression may be easily obtained.

In order to improve the balance between the long-term maintenance ability of the impression record and the recording ability of the teeth mark impression, therefore, the number-average molecular weight of the resin used for the impression recording part is more preferably in the range of 30,000 to 200,000, and is furthermore preferably in the range of 50,000 to 100,000.

iv) Glass Transition Temperature

The glass transition temperature of the resin used for the impression recording part is preferably in the range of −100 to 40° C.

The reasons are as follows. When the glass transition temperature of the resin is lower than −100° C., it may be difficult to maintain the shape at a room temperature and to maintain the impression record for a long term. On the other hand, when the glass transition temperature of the resin is higher than 40° C., it may be difficult to record the teeth mark impression accurately.

In order to improve the balance between the long-term maintenance ability of the impression record and the recording ability of the teeth mark impression, therefore, the glass transition temperature is more preferably in the range of −80 to 30° C., and is furthermore preferably in the range of −50 to 20° C.

v) Shore A Hardness

The Shore A hardness (according to JIS K6301) of the resin used for the impression recording part is preferably in the range of 30 to 80°.

The reasons are as follows. When the Shore A hardness is lower than 30°, it may be difficult to maintain the shape at a room temperature and to maintain the impression record for a long term. On the other hand, when the Shore A hardness is higher than 80°, the resin becomes so hard that it may be difficult to record the teeth mark impression accurately.

In order to improve the balance between the long-term maintenance ability of the impression record and the recording ability of the teeth mark impression, therefore, the Shore A hardness of the resin used for the impression recording part may be more preferably in the range of 40 to 75°.

vi) Melting Point

The melting point of the resin used for the impression recording part is preferably in the range of 100 to 150° C.

The reasons are as follows. When the melting point of the resin is lower than 100° C., it may be difficult to maintain the shape at a room temperature and the resin may flow easily and thereby it may be difficult to fix and stick the member into the abutment teeth etc. On the other hand, when the melting point of the resin is higher than 150° C., the resin may harden in an oral cavity and thereby it may be difficult to record the teeth mark impression accurately.

In order to improve the balance between the long-term maintenance ability of the impression record and the recording ability of the teeth mark impression, therefore, the melting point of the resin used for the impression recording part is more preferably in the range of 105 to 145° C., and is furthermore preferably in the range of 110 to 140° C.

vii) Softening Temperature

The softening temperature of the resin used for the impression part is preferably in the range of 30 to 60° C.

The reasons are as follows. When the softening temperature of the resin is lower than 30° C., it may be difficult to maintain the shape at a room temperature and the resin may flow easily and thereby it may be difficult to fix and stick the member into the abutment teeth etc. On the other hand, when the softening temperature of the resin is higher than 60° C., the resin becomes so hard that it may be difficult to record the teeth mark impression accurately.

In order to improve the balance between the long-term maintenance ability of the impression record and the recording ability of the teeth mark impression, therefore, the softening temperature of the resin used for the impression recording part is more preferably in the range of 35 to 55° C., and is furthermore preferably in the range of 40 to 50° C.

viii) Additives

Various kinds of additives also may be preferably included in the resin used for the impression recording part as well. For example, a compound or a combination of compounds, selected from the group consisting of a polymer additive, a reactive dilution agent, a radical-type polymerization initiator, a polymerization inhibitor, a polymerization initiator auxiliary, a levelling agent, a wettability modifier, a surfactant, a plasticizer, a lubricant, an ultraviolet absorber, an anti-oxidation agent, an anti-static spray, an inorganic filler, a fungicide, a gas conditioning agents a dye-dissolution agent, a buffer solution, a chelating agent, an anti-microbal agent, a perfume, and the like may be preferably used.

In order to detach the member from the teeth more easily, a lubricant or a plasticizer may be preferably included in the resin. Content of these additives in the resin for the impression recording part may be preferably higher than that in the resin for the fixing part. As the resin includes such a lubricant and a plasticizer, rigidity and creep-resistant ability are improved and thereby maintenance the quality of the impression recording part may be better.

Further, a fungicide or a perfume preferably may be included in the resin used for the impression recording part, as well as the resin used for the fixing part, in view of sanitary.

ix) Thickness

With respect to the thickness of the impression recording part, it is necessary to record the teeth mark impression of the opposing teeth. The thickness of the impression recording part is not restricted. For example, the thickness of the resin may be preferably in the range of 1 to 10 mm.

The reasons are as follows. When the thickness of the impression recording part is smaller than 1 mm, it may be difficult to record the impression record accurately and to maintain the impression for a long term. On the other hand, when the thickness of the impression recording part is larger than 10 mm, usability may become deteriorated and fabrication may become difficult.

Therefore, the thickness of the resin used for the impression recording part may be more preferably in the range of 2 to 8 mm, and furthermore preferably in the range of 3 to 7 mm.

Further, it is also preferable to determine the thickness of the resin used for the impression recording part considering the thickness of the resin used for the fixing part. For example, it is preferable that the resin used for the impression recording part is in the range of 1.2 to 5 times as thick as the resin used for the fixing part.

The reasons are follows. When the resin used for the impression recording part is smaller than 1.2 times as thick as the resin used for the fixing part, it may be difficult to record the impression record accurately. On the other hand, when the resin used for the impression recording part is larger than 5 times as thick as the resin used for the fixing part, it may be difficult to stop the movement of the impression recording part by the fixing part.

Therefore, it is more preferable that the resin used for the impression recording part is in the range of 1.5 to 4 times as thick as the resin used for the fixing part. Further, it is furthermore preferable that the resin used for the impression recording part is in the range of 2 to 3 times as thick as the resin used for the fixing part.

The size of the impression recording part is not restricted, but preferably be same as the size of the fixing part. Therefore, for example, the impression recording part may be a rectangle having 10 to 30 mm in length and 10 to 30 mm in width or a circle having 10 to 30 mm in diameter.

(3) Reflection Quality Modifier i) Kind

The kind of the reflection modifier, which is included in at least the impression recording part, is not restricted. For example, a compound or a combination of compounds, selected from the group consisting of titanium oxide, silicon oxide, aluminum oxide, zirconium oxide, indium oxide, tin oxide, zinc oxide, antimony oxide, yttrium oxide, cobalt oxide, barium sulfate, sodium sulfate, calcium carbonate, sodium carbonate, carbon, a carbon black, a glass fiber, a carbon fiber, and the like, may be used.

Among these reflection modifiers, especially titanium oxide has an excellent reflection-enhancement property and has an anti-microbial property and thereby the member is favorable in view of sanitary.

Further, among these modifiers, white-type reflection modifier, such as titanium oxide, silicon oxide, aluminum oxide, zirconium oxide and the like, is more preferable. With respect to the white-type reflection modifier, although relatively small amount of the modifier is included, excellent reflection modification effect may be obtained.

ii) Addition Amount

The reflection modifier is preferably included in the range of 0.01 to 80 weight % of the whole amount.

The reasons are as follows. When the content of the reflection modifier is lower than 0.01 weight %, it may not improve the diffusion and reflection effect of the laser light. On the other hand, when the content of the reflection modifier is higher than 50 weight %, the flowing ability of the resin used for the impression recording part and the impression recording ability may become deteriorated.

Therefore, the reflection modifier is more preferably included in the range of 0.1 to 40 weight % of the whole amount, and the reflection modifier is furthermore preferably included in the range of 1 to 30 weight % of the whole amount.

(4) Fabricating Method

Fabricating method of the teeth mark impression recording member in accordance with the first embodiment is not restricted. For example, the teeth mark impression recording member may be made by the following steps. First, by diluting the raw materials with an organic solvent, coating solutions for the fixing part and for the impression recording part are made. Then, each of these coating solutions is coated in order on a process paper (a detachable film) by using a roll coater, a gravure coater, a knife coater, a screen print processing, a bar coater, and the like.

Alternatively, the teeth mark impression recording member may be made by the following steps. First, solutions for the fixing part and for the impression recording part are coated on separate papers and dried. Then, the dried two layers are laminated by using a laminator.

[The Second Embodiment]

Figure 2:
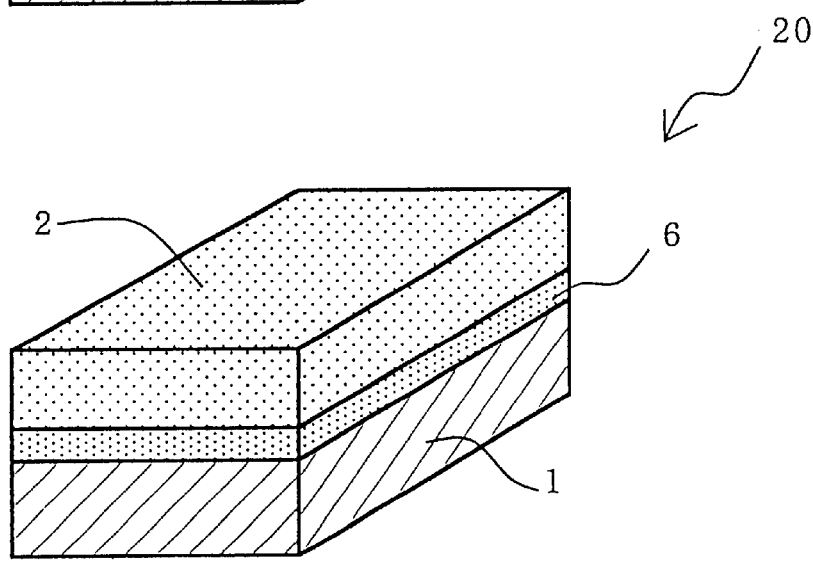
FIG. 2 shows a perspective view of the teeth mark impression recording member in accordance with the second embodiment of the present invention.

As shown in FIG. 2, the second embodiment in accordance with the present invention is the teeth mark impression recording member 20. The member 20 comprises the fixing part 1, the impression recording part 2, and the supporting part 6.

Since the teeth mark impression recording member 20 comprises the supporting part 6, size stability of the member 20 may be improved and the member may be fabricated more easily. Further, since the supporting part 6 may work as an insulator, the fixing part 1 only or the impression recording part 2 only may be locally heated and softened easily. Therefore, treatment of the teeth mark impression recording member 20 may be easier.

With respect to the resins used for the fixing part and for the impression recording part, the reflection modifier, and the like, since the description of the first embodiment may also be applicable, the description in the second embodiment will be omitted.

(1) Variety of the Supporting Part

The resin used for the supporting part is not restricted. The resin may be the resin or combination of resins, selected from the group consisting of a polyethylene resin, a polypropylene resin, a polymethylpentene resin, a (meth)acrylic resin, a silicone resin, a polyvinyl acetate resin, a polyethylene-vinyl acetate resin, a polyvinyl butyral resin, a polyvinyl formal resin, a polyvinyl alcohol resin, cellulose acetate, ethyl cellulose, a polyvinyl chloride resin, a polyester resin, a polycaprolactam resin, a polyurethane resin, a polyamide resin, a polyacetal resin, a styrene resin, a styrene-butadiene resin, a styrene-butadiene-styrene block polymer resin, a styrene-isoprene-styrene block polymer resin, a styrene-butylene-ethylene-styrene block polymer resin, a phenoxy resin, and the like.

Among these resins, a polyester resin, a polyvinyl chloride resin, a polyurethane resin, and the like, are preferable.

(2) Shape of the Supporting Part

The supporting part may be preferably a film and may preferably have a thickness of 10 to 1000 $\mu$m.

The reasons are as follows. When the thickness of the supporting part is smaller than 10 $\mu$m, mechanical strength may be deteriorated and the treatment may become difficult. On the other hand, when the thickness of the supporting part is 1000 $\mu$m or more, the tracking ability of the fixing part and the impression recording part to the teeth may be deteriorated.

In order to improve the balance between the mechanical strength and the tracking ability to the teeth etc., therefore, the thickness of the supporting part is more preferably in the range of 20 to 500 $\mu$m, and is furthermore preferably in the range of 30 to 100 $\mu$m.

Figure 3:
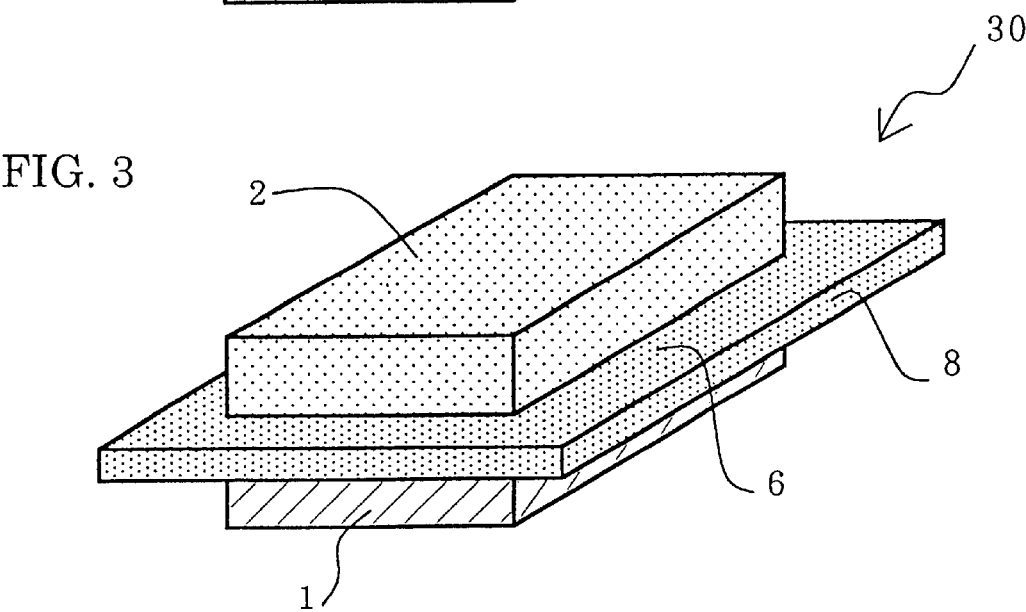
FIG. 3 shows a perspective view of the teeth mark impression recording member in accordance with another embodiment of the second embodiment of the present invention.

Further, as shown in FIG. 3, the size (area) of the supporting part 6 may be preferably larger than the size (area) of the fixing part and/or the size (area) of the impression recording part. According to the above-mentioned construction, as shown in FIG. 3, a handle 8 may be provided along the edge portions of the fixing part 1 and the impression recording portion 2. As a result, the teeth mark impression part 30 may be fixed in an oral cavity easier.

Further, due to the handle 8, deformation of the impression recording part 2 during taking out the teeth mark impression recording member 30 may be eliminated effectively. In other word, the impression recording part 2 may be detached from the opposing teeth without seizing the impression recording part 2, and then the teeth mark impression recording member 30 may be taken out from the oral cavity.

However, as the handle is too large, fixing the member 30 into the oral cavity may be difficult. Therefore, the size of the supporting part may be preferably determined considering the sizes of the fixing part and the impression recording part so that the width of the handle may become in the range of 1 to 20 mm.

Further, the supporting part may preferably be a film having holes or a net, or may preferably have a slit or a cut. According to the above-mentioned construction, deterioration of the tracking ability due to the supporting part may be prevented effectively. In addition, since the fixing part and the impression recording part are bonded partially, detaching of these portions may be prevented.

In case of the film having holes, for example, holes having a diameter of 0.1 to 1000 $\mu$m may be preferably provided so that the opening ratio (area of holes/area of film) becomes 10 to 90%. In case of the net, for example, 10 to 400 mesh may be preferably used. In case of the part having a slit or a cut, for example, each width may be preferably in the range of 0.1 to 1000 $\mu$m.

(3) Fabricating Method

Fabricating method of the teeth mark impression recording member having the supporting part in accordance with the second embodiment is not restricted as well. For example, the teeth mark impression recording member may be fabricated by using the supporting part as process paper. In other word, first, solution for the fixing part is coated on one side of the supporting part by a roll coater etc., and dried and thereby the fixing part is formed. Then, solution for the impression recording part is coated on the other side of the supporting part by a roll coater etc, and dried and thereby the impression recording part is formed.

According to the above-mentioned method for fabricating the teeth mark impression recording member, since preparing another process paper may become unnecessary, and thereby the manufacturing cost may be greatly reduced. In addition, according to the above-mentioned method for fabricating the teeth mark impression recording member, since the coating process of the solution for the impression recording part on the fixing part or the laminating process for the fixing part and the impression recording part may become unnecessary, the teeth mark impression recording member having a thickness with excellent accuracy may be fabricated.

[The Third Embodiment]

The third embodiment in accordance with the present invention is a method for using the teeth mark impression recording member. The member comprises a fixing part for fixing and sticking the member into abutment teeth and adjacent teeth, and a impression recording part for recording a impression of opposing teeth, and at least the impression recording part includes a reflection modifier.

(1) Heating Step

The heating step is the step for heating the teeth mark impression recording member at a predetermined temperature in order to soften the fixing part and the impression recording part.

As the heating apparatus, an oven, an infrared lamp, a hotplate, a water bath, a burner, and the like may be used.

The predetermined temperature, t0 which the teeth mark impression recording member is heated, may be preferably in the range of 40 to 80° C., and may be more preferably in the range of 50 to 70° C.

Since the member is heated at the above-mentioned temperature, the resin may be softened moderately and treatment may become easier. Further, since the member is not heated excessively, the teeth mark impression recording member may be maintained within a predetermined shape.

With respect to the heating step, only the fixing part of the teeth mark impression recording member may be heated locally and the resin of the fixing part may be softened. According to the above, since the impression recording part consists of the resin which may be softened easily, the part may be softened at the temperature of an oral cavity. Thus, preferably the impression recording part may not be heated to maintain the shape of the impression recording part.

Alternatively, the following steps are preferable as well. The steps are, first, only the fixing part of the teeth mark impression recording member is heated locally and the resin of the fixing part is deformed according to the abutment teeth etc. and is detached from the oral cavity. Then, only the impression recording part is softened to facilitate the recording. In the heating step, therefore, it is preferable that only the fixing part may be heated and the impression recording part is not be heated.

A temperature indicating material is preferably included in the fixing part and/or the impression recording part. As a result, heating temperature of the teeth mark impression recording member may be estimated. In other word, when the member is heated excessively, a change of color or discoloration occurs, and excessive heating may be recognized.

As the temperature indicating material, an organic dye, an inorganic dye, an organic pigment, an inorganic pigment, and the like may be used. Alternatively, as the temperature indicating material, a microcapsule with a gelatin wall including a colorant may be used. In that case, when excessive heating occurs, the wall may be destroyed and the colorant may flow outward.

(2) Recording Step for Recoding the Teeth Mark Impression of the Opposing Teeth

Figure 4:
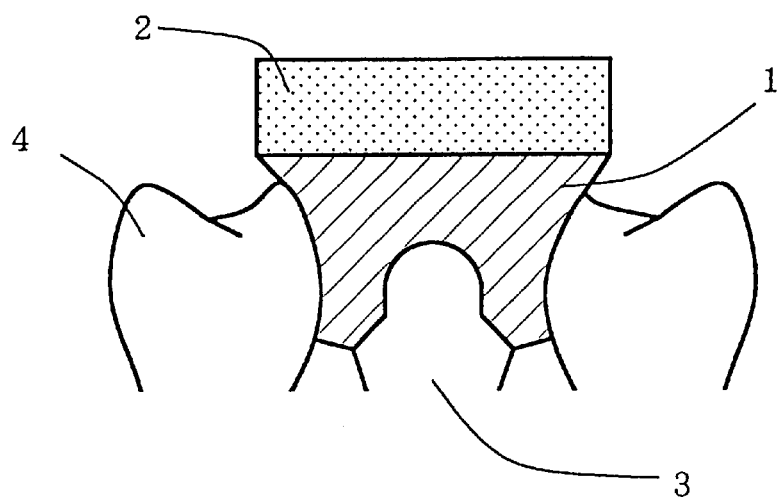
FIG. 4 shows a status in which the fixing part of the teeth mark impression recording member in accordance with the third embodiment of the present invention is fixed and stuck into the abutment teeth.
Figure 5:
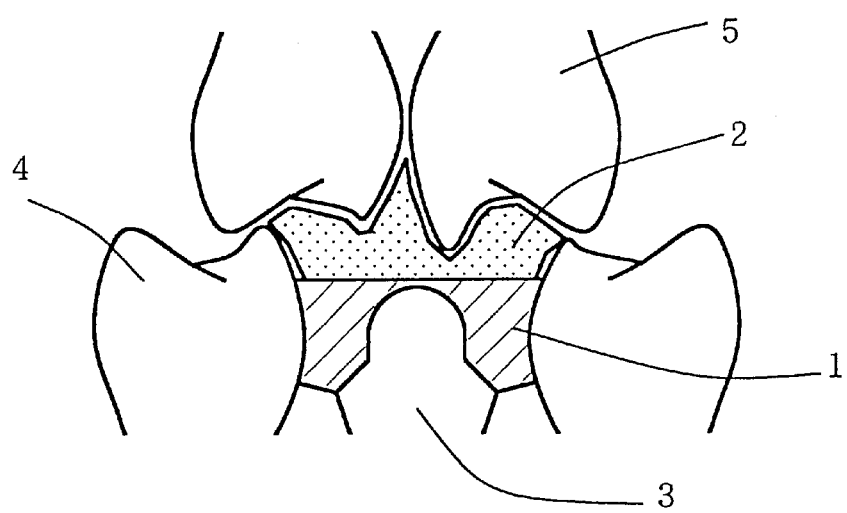
FIG. 5 shows a status in which the impression recording part of the teeth mark impression recording member in accordance with the third embodiment of the present invention is recorded as a teeth mark impression of the occlusion of the opposing teeth.

The recording step is the step for recording the impression of the opposing teeth by inserting the teeth mark impression recording member into a predetermined position such as the abutment teeth etc. in an oral cavity. Referring to FIGS. 4 and 5, a using status of the teeth mark impression recording member will be described.

Fabricating method of the abutment teeth is not restricted. The abutment teeth 3 may be formed according to the usual way with respect to the repaired premolar or molar.

FIG. 4 shows a status in which the fixing part 1 is inserted between, fixed into, and stuck into the abutment teeth 3 etc. FIG. 5 shows a status in which the impression recording part is recorded as a teeth mark impression of the occlusion of the opposing teeth. First, the teeth mark impression recording member 10 is inserted into an oral cavity and the fixing part 1 is inserted between, fixed into, and stuck into the abutment teeth 3 etc. Then, let the patient chew the teeth mark impression recording member 10 and move the member from side to side, back and forth, and thereby the teeth mark impression of the chewing state of the opposing teeth 5 is recorded to the impression recording member 2. In that case, since the fixing part 1 having high rigidity is fixed and stuck into the abutment teeth 3 etc., the movement of the impression recording part 2, which is bonded with the fixing part, may be restricted, even if the opposing teeth 5 move from side to side and back and forth. Therefore, the tracks of the opposing teeth may be recorded accurately.

(3) Measuring Step for Measuring the Teeth Mark Impression of the Opposing Teeth The measuring step is step that remove the teeth mark impression recording member from the oral cavity and measures the teeth mark impression, which was already recorded in the recording step, by using an ideal diffusion-type laser light system.

In other word, the measuring step has the following two steps. First, the teeth mark impression recording member (which may also be called "working model".) is fixed in a CAD/CAM system, which is provided with a measuring system and a processing system. Then, the laser light from the ideal diffusion-type laser light displacement system is irradiated onto the teeth mark impression, which is recorded to the impression recording part, so that the laser light is uniformly diffused and reflected and thereby the three-dimensional information may be obtained.

Since the teeth mark impression recording member includes the reflection modifier in the impression recording part, the laser light may not transmit and the laser light may be reflected omnidirectionally uniformly. Therefore, the teeth mark impression may be measured accurately.

EXAMPLES

The present invention will be described in detail according to the following examples.

Example 1

(1) Fabrication the Teeth Mark Impression Recording Member

The teeth mark impression recording member, which comprises the fixing part and the impression recording part including the reflection modifier, is fabricated in accordance with the combination described in Table 1. First, a solution for the fixing part (solution of methyl ethyl ketone) was applied on the silicon treated detachable film by using the bar coater so that the thickness of the resin becomes 2 $\mu$m. As the same manner, a solution for the impression recording part (solution of methyl ethyl ketone) was applied on the silicon treated detachable film by using the bar coater so that the thickness of the resin becomes 4 $\mu$m. Next, the resins were dried in an oven, in which the temperature is set to 70° C., for 20 minutes and thereby the coating film for the fixed part and the coating film for the impression recording part were obtained. Then, the film for the fixing part and the film for the impression recording part were laminated by using a laminator and thereby the teeth mark impression recording member was formed.

(2) Heating Step of the Teeth Mark Impression Recording Member and Recording Step First, the teeth mark impression recording member was placed so that the fixing part was opposite to the heating surface of the hotplate and heated at 60° C. Next, when the fixing part and the impression recording part were softened, the member was inserted into the teeth mark model, which was placed in the oven of 36° C. Then, the member was fixed and stuck into the abutment teeth etc. provided in the teeth mark model, and the member was pressed along the vertical direction while moving the opposing teeth all around.

When the teeth mark was recorded, the teeth mark impression recording member was fixed and stuck into the abutment teeth etc. As a result, the movement of the impression recording part may be restricted effectively, and the impression recording part may not move well as the opposing teeth move.

(3) Measuring Step of the Teeth Mark Impression Recording Member

Then, the teeth mark impression recording member was removed from the teeth mark model, and the teeth mark, which was already recorded in the impression recording part, was measured by irradiating an ideal diffusion-type laser light. As a result, the teeth mark impression, which recorded in the impression recording part, was recorded the teeth mark of the teeth mark model accurately.

Figure 6:
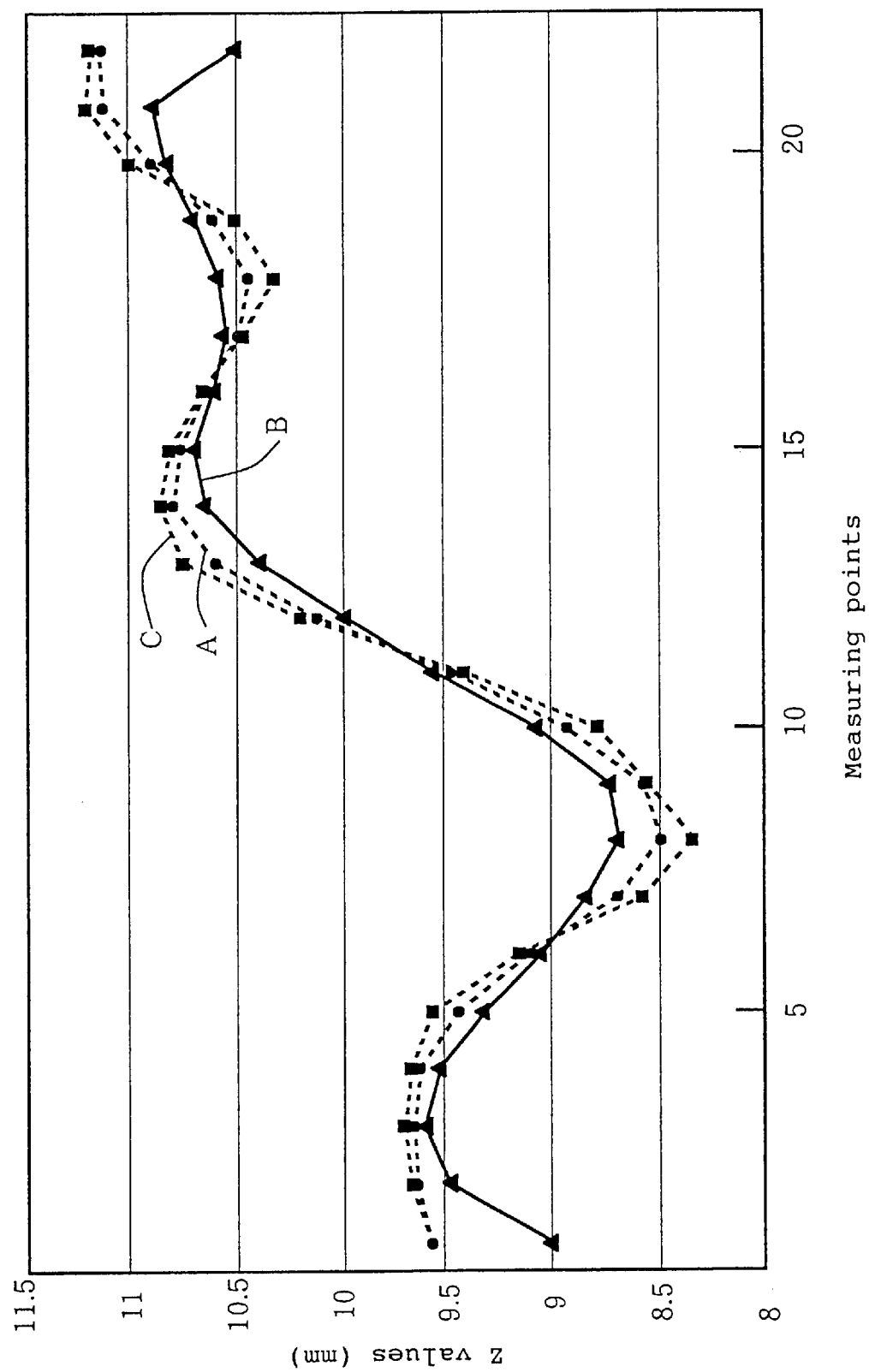
FIG. 6 shows a chart example of the teeth mark impression measured by the ideal diffusion-type laser light system.

The obtained result is shown in FIG. 6. In FIG. 6, horizontal measuring points 1 to 22 are shown in the horizontal axis and Z values (mm), which is a vertical position, are shown in the vertical axis. Also, in FIG. 6, the measuring result of Example 1 is shown as the Line A. The measuring result of Comparison Example 1, in which the resin does not include the reflection property modifier (titanium oxide) is shown as the Line B. The contact measuring result, which was measured by surface roughness, is shown as the Line C.

As easily understood in FIG. 6, since Line A and Line C have substantially the same Z value, as compared to Line B (not including the reflection modifier), the following may be said. Namely, with respect to the teeth mark impression recording member of Example 1, the teeth mark impression may be measured accurately. In other word, since the teeth mark impression recording member includes titanium oxide as the reflection modifier in its impression recording part, irradiated laser light may be uniformly diffused and reflected and thereby the teeth mark impression may be measured accurately.

TABLE 1

|  | FIXING PART (weight %) | IMPRESSION RECORDING PART (weight %) |
|---|---|---|
| Vinyl acetate polymer (Mn 150,000) | 64 | 40 |
| Ethylene-vinyl acetate copolymer (Mn 70,000) | 14 | 34 |
| Titanium oxide | 1.9 | 15 |
| Silica | 10 | 2.0 |
| Stearic acid | 10 | 8 |

TABLE 1-continued

|  | FIXING PART (weight %) | IMPRESSION RECORDING PART (weight %) |
|---|---|---|
| Blue pigments | 0.1 |  |
| Yellow pigments |  | 1 |
| Thickness (mm) | 2 | 4 |
| Grass transition temperature (° C.) | 40 | −20 |
| Shore A hardness (JIS K6301) (°) | 90 | 75 |
| Melting point (° C.) | 120 | 90 |
| Softening temperature (° C.) | 58 | 45 |

Comparison Example 1

First, a teeth mark impression recording member is fabricated as the same manner as Example 1, except for that titanium dioxide is not added to the fixing part and the impression recording part. Next, using the teeth mark impression recording member, the teeth mark was recorded and then the teeth mark recorded was measured by using the ideal diffusion-type laser light system. The result is shown in FIG. 6.

INDUSTRIAL APPLICABILITY

As described above, according to the teeth mark impression recording member in accordance with the present invention, since the impression recording part includes the reflection modifier, irradiated laser light may be uniformly diffused and reflected and thereby the laser light may not transmit, may not spread, and may not internally reflect to one direction only. Therefore, by detecting the uniform reflected light, the teeth mark impression, which is three-dimensionally recorded in the impression recording part of the teeth mark impression recording member, may be measured accurately.

In addition, since the fixing part of the teeth mark impression recording member is fixed and stuck into the abutment teeth etc., the impression recording part, which is bonded to the fixing part, may not move well as the opposing teeth move when the teeth mark impression is recorded. As a result, the teeth mark impression of the opposing teeth having excellent accuracy may be obtained. Therefore, based on the teeth mark impression, a dental crown or a dental bridge may be fabricated accurately.

What is claimed is:

1. A teeth mark impression recording member for an opposing tooth facing an abutment tooth comprising:
   a fixing part having a thickness in a range of 0.5 and 10 mm, said fixing part sticking to the abutment tooth for fixing the recording member when an impression is taken, and
   an impression recording part fixed on the fixing part for recording the impression of the opposing tooth, said impression recording part containing a reflection modifier so that irradiated light can be uniformly diffused and reflected to measure a track of the opposing tooth formed on the impression recording part.

2. The teeth mark impression recording member as recited in claim 1, wherein the reflection modifier is at least one compound selected from the group consisting of titanium oxide, silicon oxide, aluminum oxide, zirconium oxide, indium oxide, tin oxide, zinc oxide, antimony oxide, yttrium oxide, cobalt oxide, barium sulfate, sodium sulfate, calcium carbonate, sodium carbonate, carbon, a carbon black, a glass fiber and a carbon fiber.

3. The teeth mark impression recording member as recited in claim 1, wherein the reflection modifier is included in a range of 0.01 to 80 weight % of a whole amount of the impression recording part.

4. The teeth mark impression recording member as recited in claim 1, wherein said fixing part and said impression recording part are made of resins.

5. The teeth mark impression recording member as recited in claim 4, wherein the resins of the fixing part and impression recording part have glass transition temperatures, and the glass transition temperature of the fixing part is higher than the glass transition temperature of the impression recording part.

6. The teeth mark impression recording member as recited in claim 4, wherein the resins of the fixing part and impression recording part have Shore A hardnesses (JIS K6301), and the Shore A hardness (JIS K6301) of the resin used for the fixing part is higher than the Shore A hardness (JIS K6301) of the resin used for the impression recording part.

7. The teeth mark impression recording member as recited in claim 4, wherein the resins of the fixing part and impression recording part have melting points, and the melting point of the resin used for the fixing part is higher than the melting point of the resin used for the impression recording part.

8. The teeth mark impression recording member as recited in claim 4, wherein the resins of the fixing part and impression recording part have softening points, and the softening point of the resin used for the fixing part is higher than the softening point of the resin used for the impression recording part.

9. The teeth mark impression recording member as recited in claim 4, wherein each of the resins used for the fixing part and used for the impression recording part comprises;
   a high molecular weight part having a number-average molecular weight of 100,000 or greater, and
   a low molecular weight part having a number-average molecular weight of less than 100,000,
   wherein a content of the high molecular weight part, which is included in the resin used for the fixing part, is 50 weight % or greater, and a content of the high molecular weight part, which is included in the resin used for the impression recording part, is less than 50 weight %.

10. The teeth mark impression recording member as recited in claim 4, wherein temperature indicating material is included in at least or both of the fixing part and the impression recording part.

11. The teeth mark impression recording member as recited in claim 1, wherein a supporting layer is provided between the fixing part and the impression recording part.

12. A method for using the teeth mark impression recording member, comprising the steps of;
   heating the teeth mark impression recording member as recited in claim 1,
   recording tracks of the opposing tooth by inserting the teeth mark impression recording member into an oral cavity, and
   measuring the tracks of the opposing tooth, which was already recorded in the recording step, by using an ideal diffusion by laser light system.

* * * * *